United States Patent [19]

Kopatz et al.

[11] 3,998,031
[45] Dec. 21, 1976

[54] APPARATUS AND METHOD FOR THE PREPARATION OF ENCLOSED SANITARY PRODUCTS

[75] Inventors: William H. Kopatz, Levittown; Rey W. Cooper, Bryn Athyn; Russell W. Watson, Hatboro, all of Pa.

[73] Assignee: W. R. Grace & Company, New York, N.Y.

[22] Filed: May 7, 1975

[21] Appl. No.: 575,197

[52] U.S. Cl. .................. 53/124 R; 53/124 B; 53/379; 100/232
[51] Int. Cl.² .................. B65B 1/24; B65B 63/02; B65B 51/14
[58] Field of Search ......... 53/124 R, 124 B, 124 E, 53/124 TS, 39, 40, 379, 235, 249, 115, 326, 266, 267, 35, 37, 113; 100/232, 93 P

[56] References Cited

UNITED STATES PATENTS

| | | | |
|---|---|---|---|
| 319,138 | 6/1885 | Schultz | 53/326 X |
| 3,186,140 | 6/1965 | Bogdanovich | 53/124 TS |
| 3,324,902 | 6/1967 | Lense | 53/124 R |
| 3,476,037 | 11/1969 | Gorby | 53/124 TS |
| 3,748,209 | 7/1973 | Pearson et al. | 53/37 X |

*Primary Examiner*—Travis S. McGehee
*Assistant Examiner*—Horace M. Culver
*Attorney, Agent, or Firm*—Silverman and Jackson

[57] ABSTRACT

A method for the preparation of an enclosed sanitary device which comprises providing a compressible, rapidly absorptive, organic polymeric foam pre-form to which a finite length of withdrawal string has been attached, compressing said pre-form to less than about 50% of its original dry volume, and locating the compressed pre-form in fixed position within a fluid-soluble container. Additionally, said enclosed device may then be mounted upon a support and insertion structure. The apparatus for use in the method of this invention comprises means for compressing said pre-form to the dimensions of the final device and placing the resulting compressed pre-form in said container to form the enclosed device.

15 Claims, 7 Drawing Figures

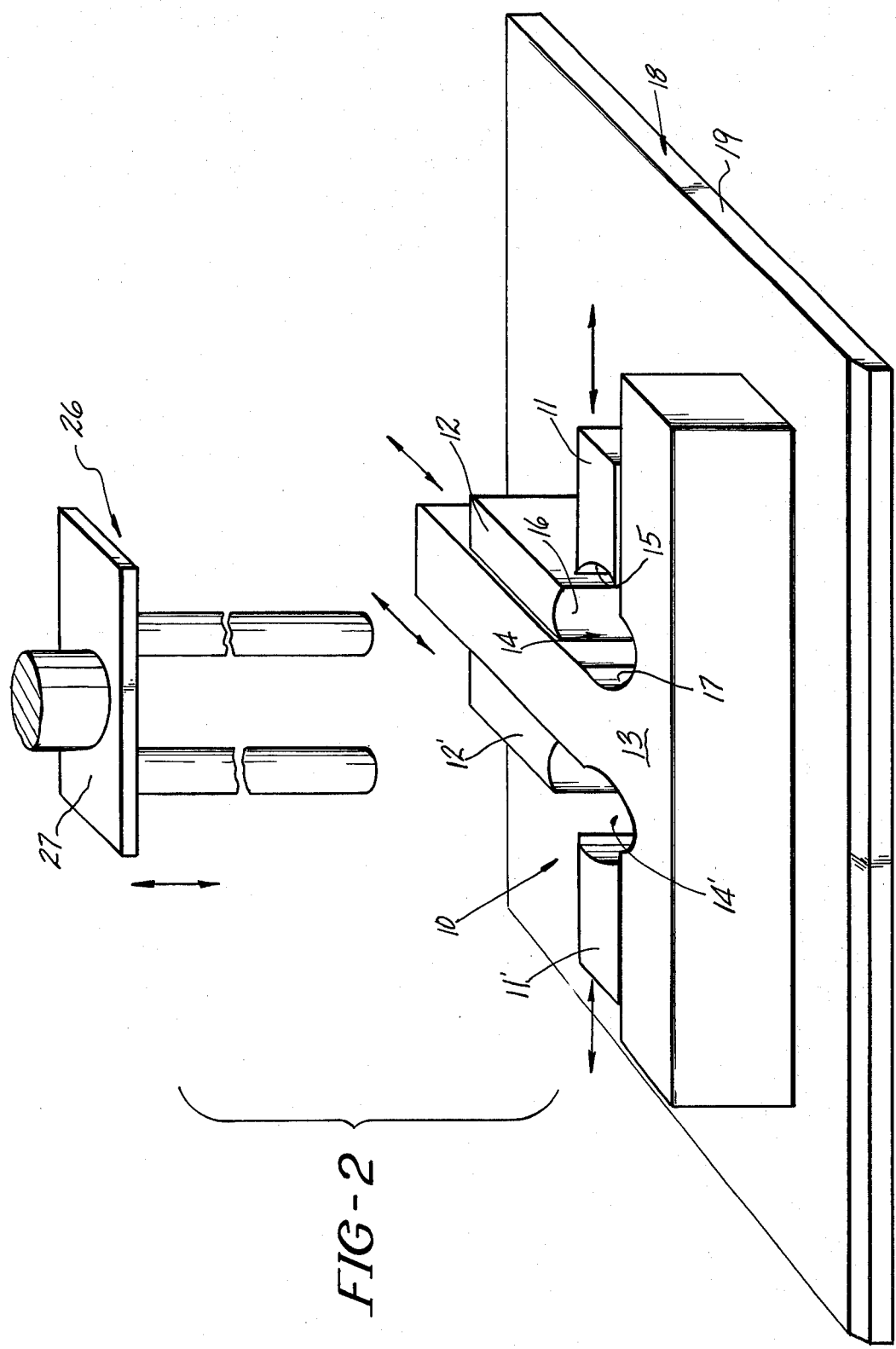

APPARATUS AND METHOD FOR THE PREPARATION OF ENCLOSED SANITARY PRODUCTS

BACKGROUND OF THE INVENTION

This invention relates to the manufacture of sanitary products such as tampons from an organic polymer foam.

Sanitary devices such as catamenial tampons have been prepared from organic polymeric foam. Such preparations usually entail the compression of the foam segment to a size suitable for insertion in the vagina and rely on various mechanical devices such as insertion tubes, for maintaining compression until insertion is completed. After insertion, the tubes are then withdrawn leaving the segment in position.

The above devices, however, possess several drawbacks. The foam segment, by virtue of its open-celled structure, is often abrasive and irritating to the vaginal membranes, which are particularly-sensitive during the menstrual period. The tampon assembly requiring the insertion tubes is cumbersome to carry and use, and consequently requires the presence of certain structural features, such as detents in both tubes to lock them in position before use, and lips or rings on the outer tube to assist in gripping during insertion. Such features are time-consuming to manufacture, and, thus, increase the cost of the final article.

In addition to the above assembly, tampons have been prepared which are mounted on insertion sticks, or are merely digitally insertable. These tampons, however, suffer from the same drawbacks and have, accordingly, been either coated or dipped with lubricants. It was found, however, that such lubricants tended to decrease the speed of absorption and absorptive capacity of the tampon, and correspondingly increase the incidence of menstural bypass.

A new class of foam materials has been discovered which yields foams possessing favorable hydrophilicity and improved expansivity. The foams comprise hydrophilic polyurethanes which are impregnated with from 10 to 200% of their weight, of a solid, water insoluble release agent which may be either an inorganic material, or a colloidal suspension of a solid organic material. These foams have been found to possess particular utility in catamenial devices, wherein they may be compressed to less than 50% of their original dry volume and placed in a constraining means, such as, for example, a gelatin capsule. The preparation of the foam containing the inorganic release agent is disclosed in the co-pending application of Louis L. Wood and Jerome L. Murray, Ser. No. 575,356, and the foam employing the organic release agent is disclosed in a co-pending application by Victor S. Frank and Jerome L. Murray, Ser. No. 575,348 both filed concurrently herewith, incorporated herein by reference.

A method for the preparation of sanitary products such as tampon devices has been developed by the Applicants herein for use with the above-referenced foams, which involves several particular operations, each employing an apparatus distinctly developed therefor. Such method and apparatus are the subject of co-pending application Ser. No. 575,200 incorporated herein by reference, and comprise the radial compression of a foam pre-form into a cylindrical die cavity of reduced diameter defined by three laterally reciprocable die faces in cooperation with a fourth stationary die face. The compressed pre-form is then axially compressed by a suitably disposed ram member and urged out of the die cavity and into a cavity defined in an adjacent base member provided with an open-ended container such as a gelatin capsule. The present apparatus and corresponding method constitute a specific embodiment of the above.

SUMMARY OF THE INVENTION

Accordingly, the present invention is an improvement over the apparatus and method disclosed in the application Ser. No. 575,200 (Attorney's Docket No. 172), for the preparation of sanitary devices such as tampons by compressing rapidly absorptive organic polymeric foam and fixedly locating said foam within a fluid soluble constraining means. Specifically, the foam which may have attached thereto a finite length of withdrawal string, is compressed to less than about 50% of its original dry volume, and is then placed within a container which may comprise a fluid-soluble material such as gelatin. The container or capsule is generally open at one end for receiving the compressed foam pre-form. As disclosed in detail herein, this opening may be constricted by the application of localized heat after the insertion of the foam, or, in an alternate embodiment, may be constricted as originally molded. The resulting enclosed device may be digitally insertable in a body cavity, or may be mounted on an insertion means which may comprise at least one tube.

The apparatus for use in the method of this invention comprises means for compressing the pre-form to the dimensions of the final device, locating the compressed pre-form within the container, and securing the pre-form within the container in fixed relation thereto.

The method of this invention provides an expeditious, lowcost assembly of an encapsulated foamed sanitary device which possesses improved lubricity and rapid reexpansion in contact with moisture such as body fluids. The device of this invention may be employed for a wide variety of sanitary and medicinal purposes, either alone or mounted upon a conventional insertion and support structure.

Accordingly, it is a principal object of the present invention to provide a method for the preparation of sanitary devices comprising compressing an absorptive organic polymeric foam pre-form, and constraining said pre-form within a fluid-soluble container.

It is a further object of the present invention to provide a method as aforesaid which is capable of practice on a mass production basis and which yields products of uniform, high quality possessing improved lubricity and reduced irritation.

It is a still further object of the present invention to provide an apparatus for the production of sanitary devices in accordance with the method as aforesaid which may be operated at high speed and accuracy.

Other objects and advantages will be apparent to those skilled in the art from a consideration of the description which follows with reference to the accompanying figures.

BRIEF DESCRIPTION OF THE DRAWINGS

FIG. 2 is a schematic perspective illustrating the spatial arrangement of the elements of the die.

DETAILED DESCRIPTION

Figure 1:
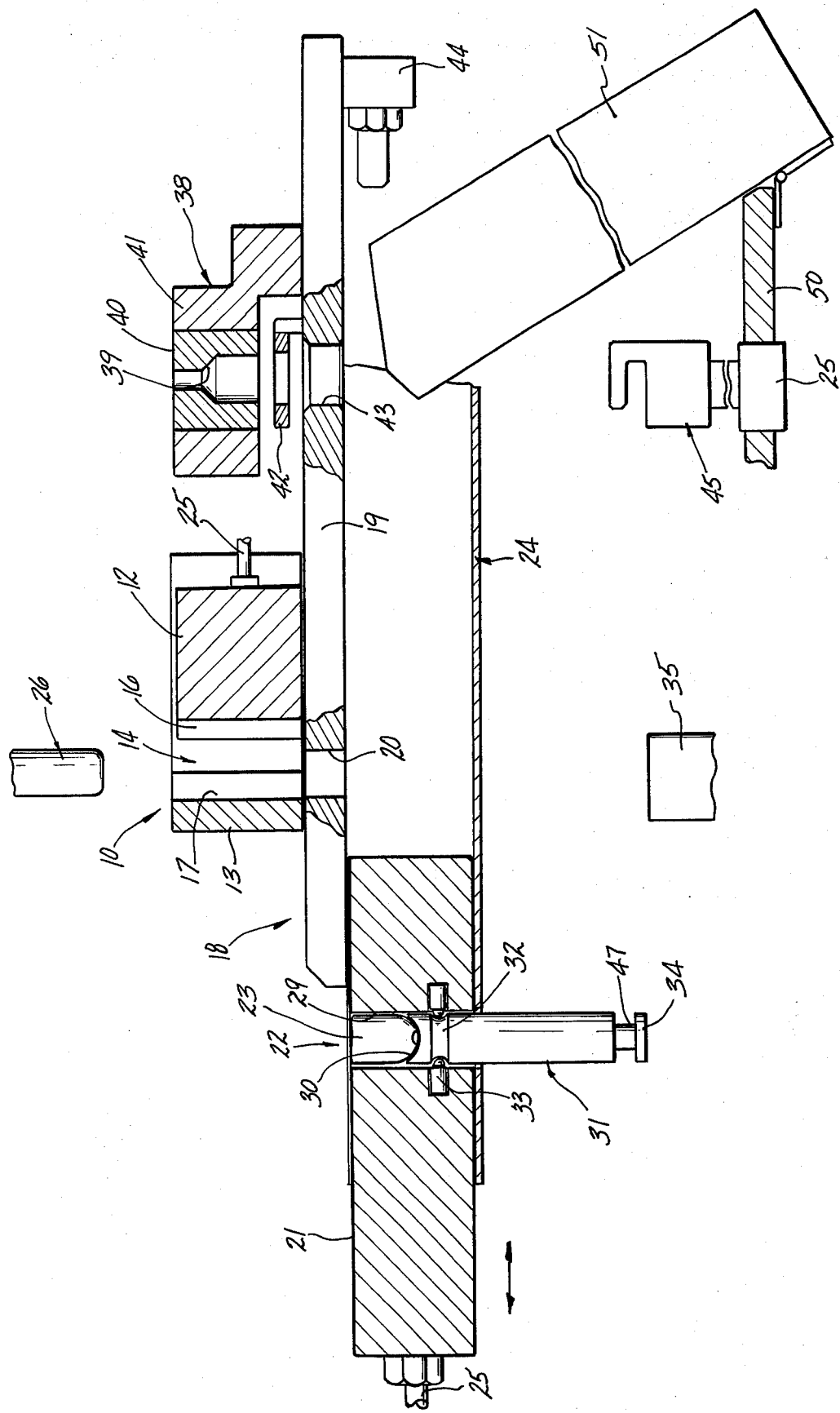
FIG. 1 is a side view partly in section illustrating the apparatus of the invention.

In accordance with the present invention, the foregoing objects and advantages are readily obtained.

The invention comprises a method and apparatus for the preparation of an enclosed sanitary device from a compressible, rapidly absorptive organic polymeric foam. The method comprises providing said foam in a predetermined shape or pre-form having attached thereto a finite length of a withdrawal string, compressing said pre-form with said string attached to less than about 50% of its original dry volume, and locating said compressed pre-form in fixed position within a container such as a fluid-soluble capsule. Optionally, the device which may comprise a tampon, may be mounted upon an insertion and support structure such as, for example, one or more insertion tubes. The method of this invention is capable of fully automated operation in a manner which is both commercially and hygienically expeditious.

As noted earlier, the foam employed in the pre-form of this invention preferably comprise hydrophilic polyurethane materials which are impregnated with from 10 to 200% of their weight, of a solid water insoluble release agent which may be either an inorganic material or a colloidal suspension of a solid organic material, all in accordance with Ser. Nos. 575,356 and 575,348 referenced above. As noted in said application, the foam materials disclosed therein possess unexpectedly improved reexpansion capability and resistance to the deleterious phenomenon known as compression set. Further in accordance with the above-referenced applications, it was surprisingly discovered that said foams could be constrained within a container such as a gelatin capsule of appropriate dimensions which would constrain said foam in a compressed state before insertion in a body cavity, and would rapidly dissolve once inserted to permit said foam to rapidly expand into contact with the walls of said cavity.

The shaping of the foam pre-form, and the attachment, if desired, of a finite length of string thereto may be conducted in any of several ways constituting conventional procedures in the art, as well as the techniques disclosed and claimed in application Ser. No. 575,200. Also, as disclosed in all of the above-referenced applications, the foam pre-form may be of variable dimensions, but for the purposes of tampon manufacture, it is preferably prepared to measure about 1 × 1 × 2 inches, the larger dimension received in the longitudinal direction.

In accordance with the invention, the pre-form is compressed within an apparatus broadly comprising a cylindrical die composed of a plurality of laterally reciprocable die faces situated upon a base member possessing an orifice therein for the engagement of a container by the compressed pre-form. A ram member is situated in axial alignment with the cavity defined by said die, and is adapted to telescopically engage the die cavity and axially urge the pre-form out of the die and into the container.

Referring now to the figures, a preferred embodiment of the apparatus of the present invention is disclosed in detail. Die member 10, as illustrated in schematic in FIG. 2, comprises laterally reciprocable die faces 11 and 12, and corresponding mirror-image die faces 11' and 12', respectively. In the figure, the die member is adapted for the simultaneous compression of two pre-forms, and the modification to enable the compression of a greater number of pre-forms may be readily envisioned by those skilled in the art. Thus, instead of providing two laterally opposed die faces and a perpendicularly opposed die face to define a single die cavity, respective die faces 11, 12, 11' and 12' meet with the symmetrical mating surfaces provided by stationary T-shaped die face 13 to define identical die cavities 14 and 14', respectively.

Figure 3A:
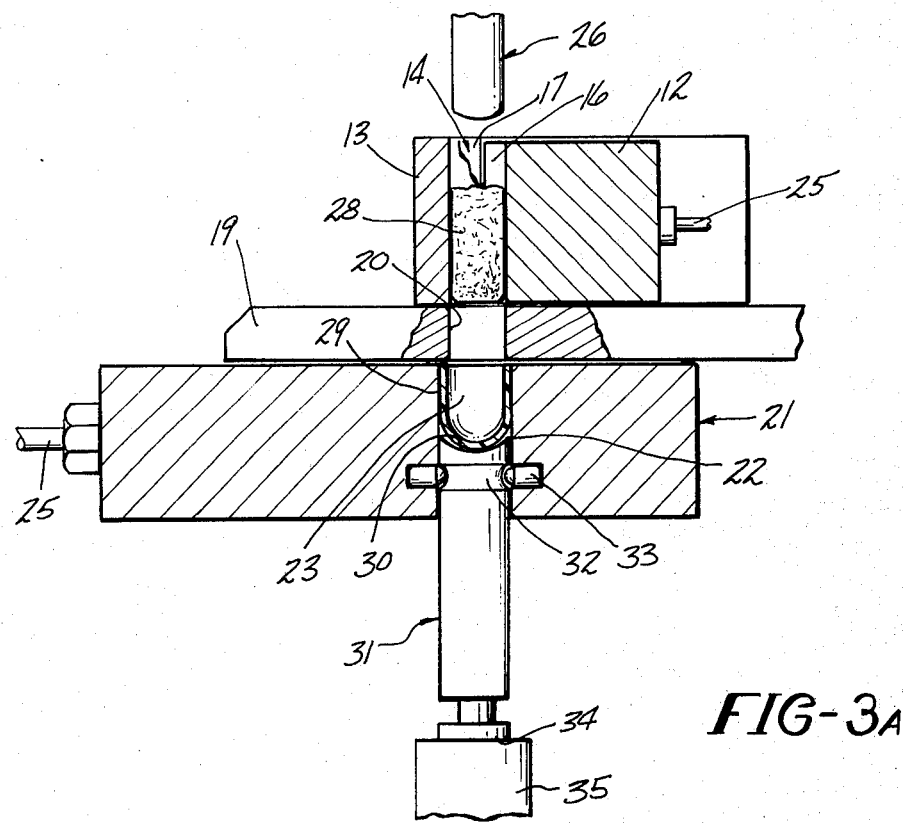
FIG. 3A is a view similar to FIG. 1 showing a preform in compression within the die.
Figure 3B:
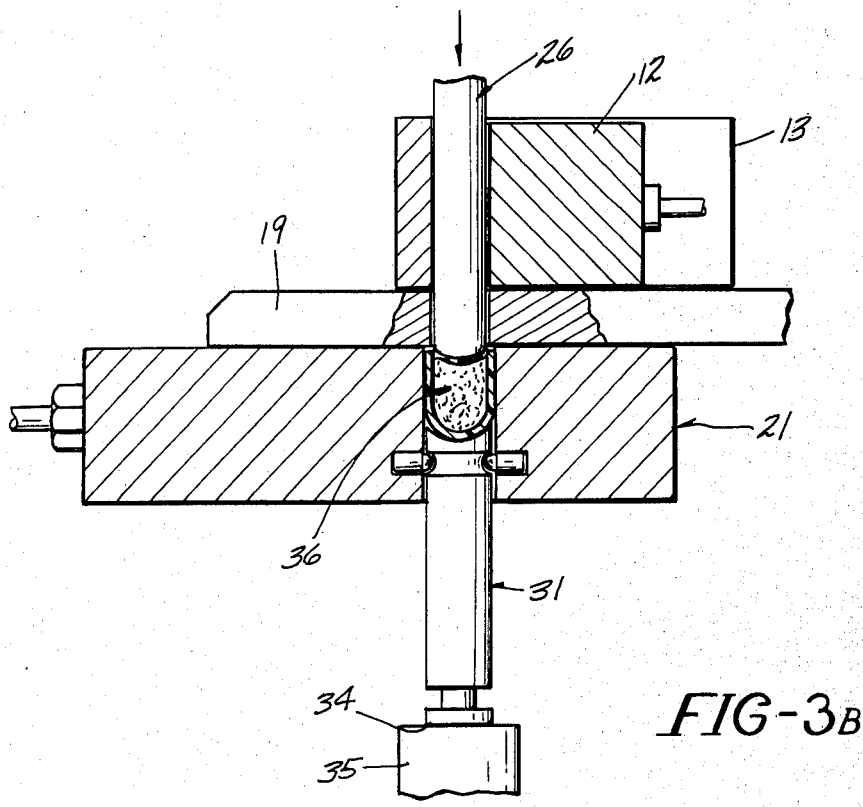
FIG. 3B shows the pre-form of FIG. 3A axially urged into a container to form the enclosed device.

In FIGS. 1 and 2, die member 10 is shown in the open position, in preparation for receiving a foam pre-form, and inner die surfaces 15, 16 and 17 of die faces 11, 12 and 13 are apart and do not define a cylindrical cavity. In FIGS. 1, 3A and 3B, die face 11 is deleted to enable the illustration of cavity 14 in both the open and the closed position.

Die member 10 rests upon base member 18 which includes stationary base plate 19 to which die face 13 is affixed. Die faces 11 and 12 are reciprocable and would be supported by rails or the like, not shown, in a manner conventional in the art. Base plate 19 possesses fixed opening 20 aligned with cavity 14 and of equal dimension to cavity 14 in the closed position, for the passage of a compressed pre-form into engagement with a container.

Base member also includes slidably reciprocable carriage member 21 which is provided with receptacle 22 for supporting a container such as capsule 23 depicted in FIG. 1. Receptacle 22 is of a size proper to accomodate a container of an internal diameter equalling that of opening 20. In practice, a capsule is placed within receptacle 22 and carriage member 21 is advanced into position below die member 10 so as to align opening 20 and capsule 23. Carriage member 21 may be supported by a structure such as rails 24 illustrated in FIG. 1 only, which may, if desired, be attached to base plate 19 or another conventional supporting structure. Carriage 21 as well as other moving parts, such as die faces 11 and 12, etc., may be actuated by any of several means, not shown, which are well known in the art, such as, for example, electric motors, pneumatic pumps and the like, and structures labeled 25 herein are to be considered representative of all actuating means within the scope of the invention.

In addition to die member 10 and base member 18, the apparatus of the present invention includes an axially aligned ram member schematically depicted in the figures and labeled 26. In the embodiment of FIG. 2, ram member 26 would comprise dual aligned ram members joined by common bridgehead 27 and actuated by a common means. Ram member 26 is adapted for axial extension into telescopic engagement with die cavity 14 during the compression of a pre-form, to axially compress said pre-form and urge it through the opening in base plate 19 and into an awaiting capsule.

Referring to FIG. 3A, the first stage in compression of a pre-form is illustrated. Pre-form 28, depicted as cut to a size appropriate for tampon manufacture and provided with a withdrawal string for purposes of illustration only, is under compression in die 10 and is shaped to a cylinder in conformity with die cavity 14 defined by converged inner surfaces 16 and 17. Ram member 26 is about to descend to force pre-form 28 into axial compression toward opening 20. Carriage 21 bearing capsule 23 in receptacle 22 has indexed into axial alignment with die cavity 14 and opening 20 to receive pre-form 28.

Receptacle 22 is composed of side wall 29 defined by carriage 21 and concave end wall 30. End wall 30 is placed at one end of rod-shaped support member 31 which is provided to enable the ejection of the resulting enclosed device from receptacle 22. Thus, in the crimping operation discussed later, support member 31 is axially elevated to place the device in contact with a crimping means. During the compression of preform 28 and its location within capsule 23, support member 31 is fixed in position within carriage 21 by the cooperation of an annular detent 32 with spring-loaded engagement means 33 provided in side wall 29. Since engagement means 33 retracts in response to a minimal amount of force to allow the movement of support member 31 during subsequent operations, the distal end 34 of support member 31 is positioned against brace 35 during the compression operation to prevent any downward movement.

Referring to FIG. 3B, upon the complete extension of ram member 26, pre-form 28 is forced into location within capsule 23, and the enclosed sanitary device 36 is thereby formed.

Figure 4A:
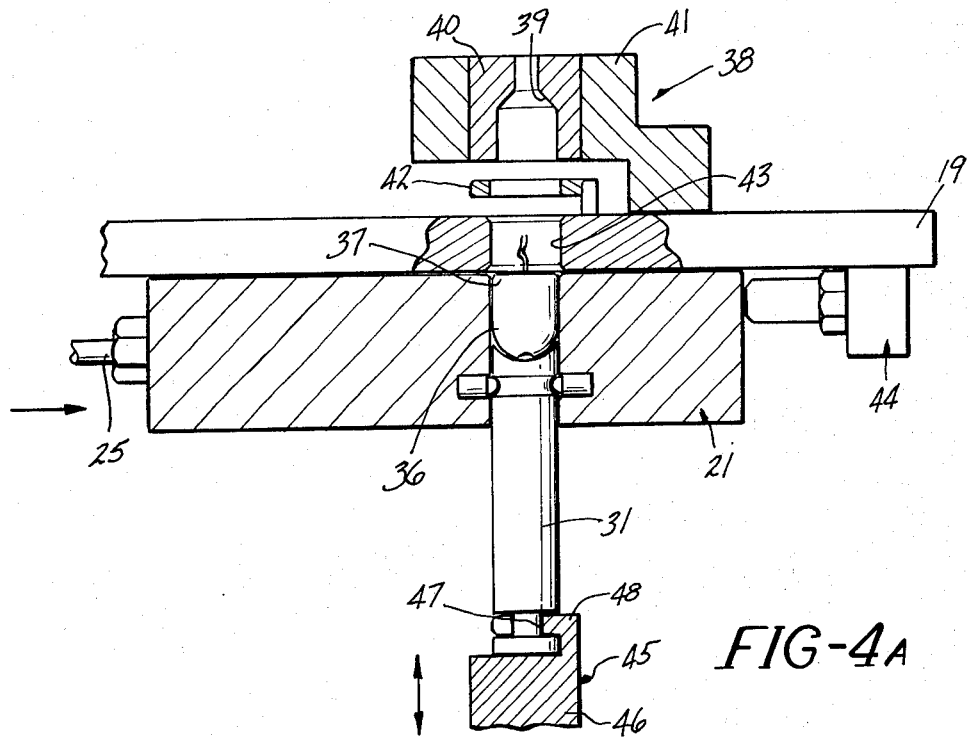
FIG. 4A is a side view partly in section illustrating the enclosed device aligned for entry into the crimping means.

In order to prevent the foam of pre-form 28 from escaping from container 23, the circumference 37 of the open end of device 36 is preferably constricted or crimped by a subsequent operation. Referring to FIG. 4A, device 36 is conveyed within receptacle 22, to a crimping station where circumference 37 is decreased by the application of localized mechanical pressure and heat. Crimping assembly 38 comprises a tubular cavity 39 of decreasing diameter defined by a heat source 40 such as a resistance heating element. Naturally, the invention should not be limited to this form of heating as various heating means such as microwave and laser energy exist which would be readily adaptable within the skill of the art. Heat source 40 is held in position by support structure 41 which is suitably attached to base plate 19. In addition to the heating means disclosed above, crimping assembly 38 includes retaining structure 42 for holding device 36 in position during the crimping operation.

Referring again to FIG. 4A, carriage 21 is aligned with tubular cavity 39 to enable the direct ascent of device 36. Likewise, base plate 19 is provided with a second opening 43 in alignment with cavity 39 for the passage of device 36. Carriage member 21 is assured of alignment with second opening 43 by the presence of stop 44 affixed to the underside of base plate 19.

Figure 4B:
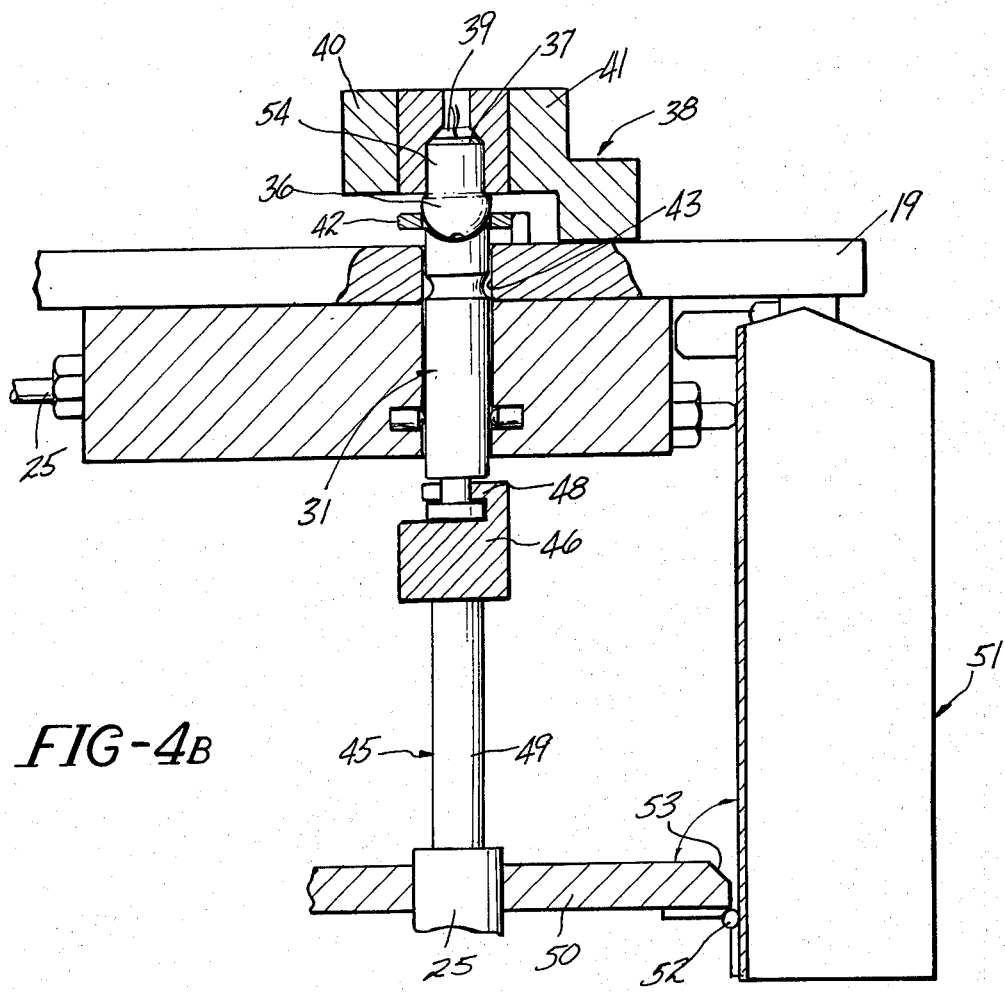
FIG. 4B shows the device of FIG. 4A after completion of the crimping operation.

In FIG. 4B, device 36 is illustrated in position within heat source 40. Elevation is achieved by the exertion of axial force upon support member 31 by elevation means 45 comprising slotted head member 46 adapted for engagement with annular constriction 47 which is distally located on support member 31. When carriage member 21 indexed into alignment with crimping assembly 38, head member 46 engaged constriction 47 with a forklike slotted protrusion 48.

Figure 5:
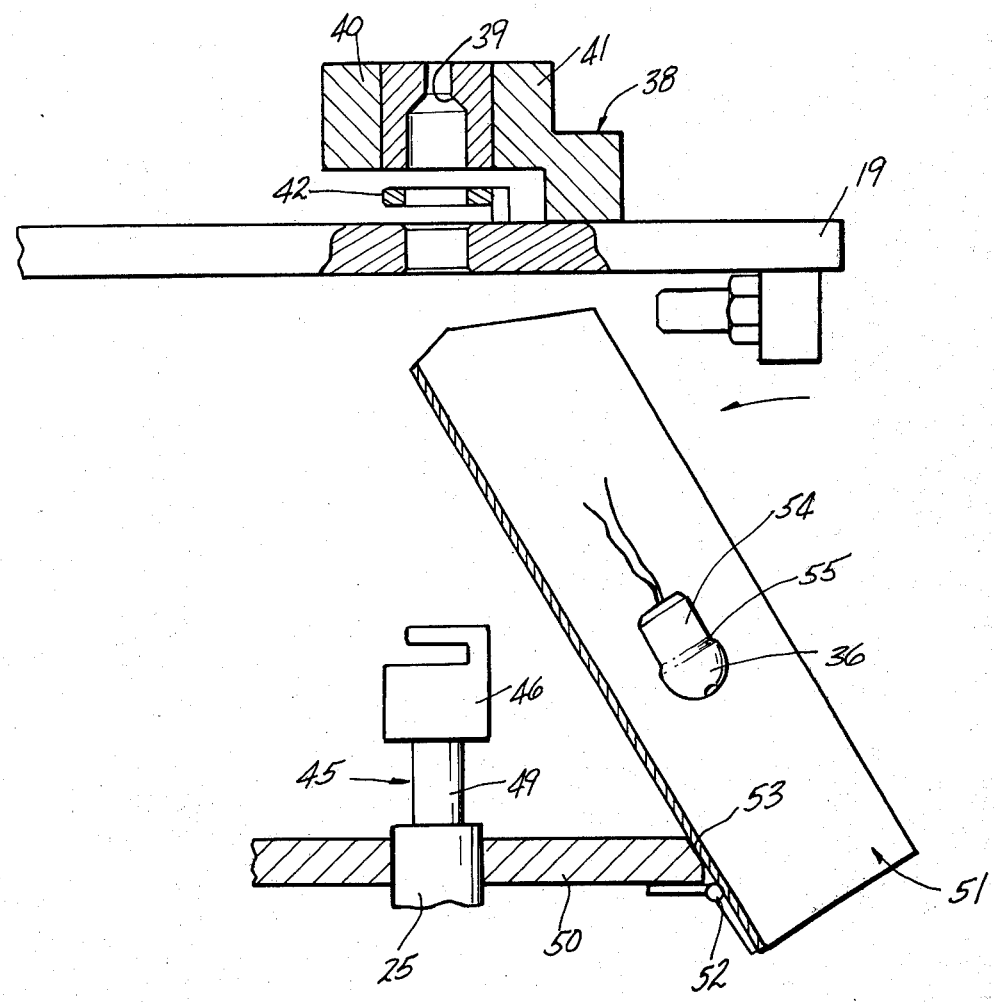
FIG. 5 is a side view partly in section showing the ejection of the final enclosed device.

Elevation means 45 is provided with motive power through extending arm 49 by a conventional reciprocating actuating means 25 located in a lower support structure 50. Support structure 50, which may comprise a part of the framework supporting the apparatus above the ground, also provides support for pivoting chute 51 which is attached thereto by hinge 52. During the crimping operation, chute 51 is maintained in the vertical position away from opening 43, by the presence of carriage 21, as shown in FIG. 4B. Upon completion of the crimping operation, as seen in FIG. 5, elevation means retracts bringing support member 31 back to the position shown in FIG. 4A, and carriage 21 indexes back to the position shown in FIG. 1, permitting chute 51 to assume an inclined position, resting on beveled end 53 of structure 50. Retaining structure 42 releases crimped final device 36 which then drops into chute 51 to an appropriate collection means, not shown.

As noted earlier, the device of this invention, if used as a tampon, may be employed alone for digital insertion, or may be mounted upon a wide variety of well known insertion means. The manner of mounting and types of insertion structures are fully developed in co-pending application Ser. No. 575,200 and the disclosure of same is incorporated herein. Further in this regard, the outer configuration of the device should be noted, for, as illustrated in FIGS. 4B and 5, the device 36 emerges from crimping assembly 38 reduced in diameter over at least a portion of its length. Thus, device 36 possesses a reduced diameter 54 which may extend to a large portion of its overall length and which meets with the original diameter at necked region 55. This configuration is useful in the instance where the device is to be mounted on a tubular support structure, as such structure can be selected which permits device 36 to nest in one end thereof and to retain its position due to the engagement of said tubular structure with necked region 55.

The device described above may be employed for a wide variety of medicinal and sanitary purposes, such as tampons and hemhorroidal suppositories, and may also contain, as desired, various suitable additives such as deodorants, disinfectants, perfumes, medicaments, emollients, pigments and/or dyes. In a further embodiment, the device may be employed to test for the presence of various microorganisms by the incorporation of a suitable chemical indicator. Naturally, the size and shape of the device of this invention may vary widely to account for variations in locus of use and functions. Likewise, a wide variety of suitable containers may be employed in addition to the gelatin capsule illustrated herein. Thus, a capsule may be employed which is initially formed with a constricted or crimped circumference, and the method and apparatus disclosed herein would be modified by the deletion of the crimping operation.

It is understood that the invention is not limited to the illustrations described and shown herein which are deemed to be merely illustrative of the best modes of carrying out the invention, and which are susceptible of modifications of form, size, arrangement of parts and details of operation, but rather is intended to encompass all such modifications which are within the spirit and scope of the invention as set forth in the appended claims.

What is claimed is:

1. An apparatus for the compression and enclosure of a foam pre-form to prepare an enclosed sanitary device which comprises:
   A. at least one die member comprising a plurality of laterally reciprocable die faces cooperating with a stationary die face to define a cylindrical die cavity of reduced diameter, said die member adapted to radially compress a pre-form placed therein into a cylindrical shape;

B. a base member comprising a stationary base plate directly adjacent one end of said die member, and a reciprocable carriage member slidably engaging said base plate, said base member possessing an orifice comprising a stationary opening located within said base plate in fixed alignment with said die cavity, and a receptacle located in said carriage comprising a cylindrical side wall defined by said carriage and a concave movable end wall defined by an axially reciprocable container support member, said receptacle providing a cavity for supporting a container, and said orifice aligned with said die cavity for the engagement of said pre-form with said container; and C. at least one ram member adjacent the opposite end of said die member and in axial alignment therewith adapted to telescopically engage said die cavity and axially urge said pre-form into said container to form said device.

2. The apparatus of claim 1 including means for maintaining said end wall and said side wall in fixed relation.

3. The apparatus of claim 2 wherein said maintaining means comprises an annular detent proximally adjacent said end wall on said support member, and a spring-loaded engagement means provided in said side wall communicating therewith.

4. The apparatus of claim 3 further including a bracing means structurally integrated with said base member for maintaining said support member in a fixed position during the compression of said pre-form.

5. The apparatus of claim 1 further comprising means for securing said pre-form in position within said container.

6. The apparatus of claim 5 wherein said securing means comprises a crimping station located adjacent said die member.

7. The apparatus of claim 6 wherein said crimping station comprises a crimping assembly fixedly mounted on said base plate.

8. The apparatus of claim 7 wherein said crimping assembly comprises a tubular cavity of reduced diameter containing a localized heating means.

9. The apparatus of claim 8 wherein said heating means comprises a resistance heating element.

10. The apparatus of claim 7 wherein said crimping assembly further includes means for locating said device within said crimping assembly.

11. The apparatus of claim 10 wherein said locating means comprises a second opening provided in said base plate in alignment with said crimping assembly and means cooperating with said support member for elevating said device through said second opening and into engagement with said assembly.

12. The apparatus of claim 11 further including means for receiving the crimped device.

13. The apparatus of claim 12 wherein said receiving means comprises a chute pivotally movable in and out of alignment with said second opening.

14. The apparatus of claim 1 further including a plurality of actuating means whereby all major moving parts thereof are provided with power actuation.

15. The apparatus of claim 14 wherein said actuation means comprise a plurality of pneumatic cylinders.

* * * * *